United States Patent [19]
Wijay

[11] Patent Number: 6,004,339
[45] Date of Patent: *Dec. 21, 1999

[54] BALLOON CATHETER WITH MULTIPLE DISTENSIBILITIES

[75] Inventor: Bandula Wijay, Houston, Tex.

[73] Assignee: AngioDynamics Incorporated, Queenbury, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/748,295

[22] Filed: Nov. 13, 1996

[51] Int. Cl.$^6$ .................................................. A61M 29/00
[52] U.S. Cl. ............................................. 606/192; 604/96
[58] Field of Search .......................... 606/108, 191–200; 604/96–104; 600/201, 204, 207

[56] References Cited

U.S. PATENT DOCUMENTS

| | | | |
|---|---|---|---|
| 5,348,538 | 9/1994 | Wang et al. | 606/192 |
| 5,447,497 | 9/1995 | Sogard et al. | 604/101 |
| 5,554,120 | 9/1996 | Chen et al. | 604/96 |
| 5,645,789 | 7/1997 | Roucher | 604/96 |

*Primary Examiner*—Glenn K. Dawson
*Attorney, Agent, or Firm*—Rosenblatt & Redano P.C.

[57] ABSTRACT

A balloon is disclosed that has two differing rates of distensibility. It can be used to perform angioplasty by taking advantage of its high strength and relatively low distensibility up to a predetermined range of pressure and still be used to set a stent by operating a pressure range where there is a higher distensibility. the balloon can be of a single material that is oriented less than fully or a blend of materials similarly oriented. In another embodiment, strands of a more crystalline material run longitudinally through a matrix of a less crystalline material, with the resulting balloon, when not fully biaxially oriented, exhibiting high burst strength and two different rates of distension at different applied inflation pressures.

16 Claims, 5 Drawing Sheets

BALLOON CATHETER WITH MULTIPLE DISTENSIBILITIES

This application is a continuation of copending application Ser. No. 08/748,295, filed on Nov. 13, 1996.

FIELD OF THE INVENTION

The field of the invention relates to balloons for medical devices, as well as the principles and processes of making such balloons from polymeric materials.

BACKGROUND OF THE INVENTION

Balloons are often used to dilate constricted tubular body cavities such as arteries, veins, urinary cavities, etc. Basically, a balloon is attached to a tubular catheter body with a facility to inflate such balloon using liquid media. Specifically, balloons are used in various angioplasty procedures such as coronary angioplasty, peripheral angioplasty, dilation of the esophagus and ureter and other urological cavities.

In the recent past, stents have been used to maintain patency of lumens that have been dilated by angioplasty balloons. Stents are medical devices made of metal or plastic material but essentially scaffold the lumen of the body cavity. Several stents, such as one made by Johnson & Johnson of New Jersey, have been used to maintain patency of the lumens so dilated by angioplasty balloons.

It is often necessary to use a balloon not only to place such metal stents in the required location but also to distend the stent so that the stent is well pressed into the tissue of the said body cavity. To press such metal stents to the body cavity requires very high pressure. For stents placed in the coronary artery, normal pressure required is between 15–20 atm. Different stents manufactured by different manufacturers require different pressures to press the stent to the body cavity.

Angioplasty balloons, dilation balloons, in general, are made from polyvinyl chloride, irradiated polyethylene, polyethylene terapthylate, polyamide, polyurethane, and from another host of polymers that can be biaxially oriented to impart strength. It is well-known in the art that a polymeric material that has been formed with a given shape, such as a tube, by melt processing can be subsequently processed to impart higher tensile strength by stretching. By stretching, the molecular structure of the polymer is oriented so that the strength in that direction is higher. In a typical process of making a balloon, a polymeric tube such as nylon of polyethylene terapthylate (PET) is extruded into a tube form first. The tube is subsequently heated to a temperature close to its glass transition temperature at which the tube softens and, by pressurizing the tube from inside, a bubble or balloon is formed. When this operation is carried out in a mold, a predetermined shape of balloon of a given size can be made. Sometimes it is necessary to stretch the tube in a lengthwise direction in order to orient the molecules in the lengthwise direction. This type of operation causes what is known as biaxial orientation. Balloons have been formed as early as 1977 by others for medical devices by biaxial orientation.

Biaxial orientation and the degree of biaxial orientation can be measured by studying the birefringence of the part so formed.

When balloons are formed from PVC, irradiated polyethylene (I-PE), polyethylene terapthylate (PET) or nylon (PA), polyurethane (PU) or others, in order to impart high strength as measured by its burst pressure, it is necessary to as fully as possible biaxially orient the molecules. Most balloons formed by biaxial orientation are, however, distensible. Distensible means that a balloon formed to a certain diameter (d) at a working pressure (p) will slightly grow in its diameter when the pressure is increased. Polyethylene, PVC, PU, and nylon balloons grow well over 10% of its diameter when the pressure is increased by 5–10 atm. On the other hand, PET grows very slightly, often less than 10%.

There are some advantages and disadvantages of distensibility. On one hand, when a balloon is distensible, especially at low pressure, 5–10 atm, it can cause damage to the body cavity or artery as the excessive distension will break, or damage unaffected tissue in the arterial wall. Such damage made during a procedure has been found to be the main cause for restenosis of the artery due to scar tissue formation. Most of the balloons that are distensible, when once expanded beyond their yield point, due to the nonreversibility of the process, are bulky. Polyethylene and nylon balloons, when once expanded, remain quite bulky and do not return to the original thin profile set at the time of manufacture of the balloon.

The other disadvantage, and the most important of all, is the fact that these distensible balloons distend at all pressures. In other words, the distensibility is uniform and happens even at lower pressures. The balloon starts growing its diameter from 2–20 atms in a uniform manner.

Nondistensible balloons, i.e., balloons that are distensible less than 10% of its diameter, such as PET balloons, have the advantage of high tensile strength and have very high burst pressure. These can also be made in very thin wall so that the balloon profile is quite small when folded over the catheter tube. These balloons can be made from material having different molecular weight and molecular weight distribution. Often the molecular weight characteristic is measured by the intrinsic viscosity of the material. Depending on the intrinsic viscosity of the PET polymer used, one will be able to make a very strong or less strong balloon. But in either case, the balloon is nondistensible.

An object of the present invention is to provide a balloon that is strong and that has at least two differing rates of distensibility so that a single balloon can be used effectively for angioplasty as well as to set a stent. In angioplasty, the increased distensibility at higher pressures allows use of a given balloon that is for example 3 mm in an artery that is somewhat larger such as 3.3 mm. The same catheter can be used in the angioplasty and later to deliver and set a stent. Alternatively, the balloon can carry a stent and the angioplasty can be performed by use of a first pressure. By then raising the pressure, the stent is pressed into the tissue to its set position.

SUMMARY OF THE INVENTION

A balloon is disclosed that has two differing rates of distensibility. It can be used to perform angioplasty by taking advantage of its high strength and relatively low distensibility up to a predetermined range of pressure and still be used to set a stent by operating a pressure range where there is a higher distensibility. the balloon can be of a single material that is oriented less than fully or a blend of materials similarly oriented. In another embodiment, strands of a more crystalline material run longitudinally through a matrix of a less crystalline material, with the resulting balloon, when not fully biaxially oriented, exhibiting high burst strength and two different rates of distension at different applied inflation pressures.

DETAILED DESCRIPTION OF THE PREFERRED EMBODIMENT

Figure 1:
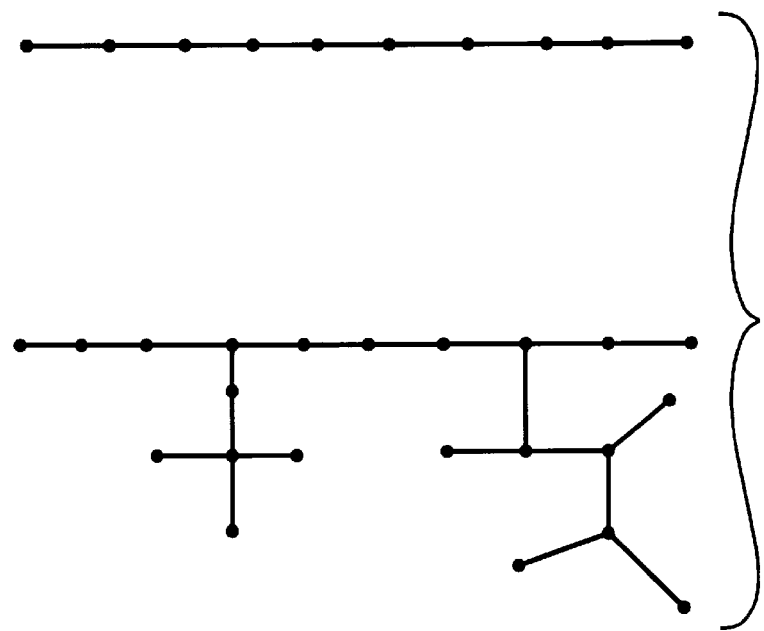
FIG. 1 is a representation of straight chain and branched chain polymers.

In this invention, a method is described to make a balloon that is not only strong (15–25 atm burst strength) but has certain distensibility characteristics. Before this invention is described, it is necessary to explain the principles involved. Polymer molecules are very large structures, compared to simple molecules such as water, alcohol, or sugar. These molecules can be straight chain or branched (see FIG. 1).

Figure 2:
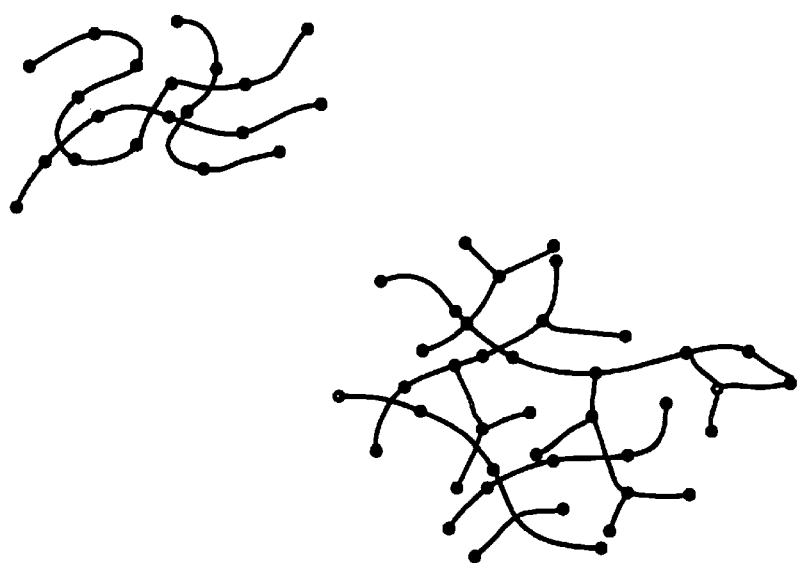
FIG. 2 is a representation of the random nature of polymers.

However, in a normal polymer structure that has been melt-processed, the molecules are random, whether they are straight chain or branched chains (see FIG. 2).

During orientation, uniaxially (by stretching in one direction) or biaxially (by stretching in two directions such as in making balloons), the polymer molecules are stretched and aligned into its stretched axial direction. Molecules then orient to this direction, imparting strength. Often the material transforms to crystalline structure. The degree of crystallinity will also determine the strength.

After orientation, polyethylene and nylon, which are amorphous, become relatively crystalline. Relatively, that is, and the portions that are not crystalline give rise to the excessive distensibility seen in these materials. Polyethylene terapthylate, on the other hand, orients quickly and often becomes crystalline. The degree of crystallinity is very high but with low distensibility.

The present invention describes a means to alter this behavior of the material in two ways. In the past, many inventors have tried to blend different materials to combine these two properties to design a balloon that has strength (20+ atm. burst) when the wall thickness is 0.0005". However, when materials are just blended, one will still obtain a balloon that is distensible starting at low pressure (5 adm. and up). On the other hand, PET and nylon do not blend very well due to differences in their chemical nature and difference in melting points. I have blended PU and PET and the resulting balloons still have properties of PET balloons or have very poor burst strength when the percentage of PU is higher than 20%.

In this invention I have determined a process by which I can stop the degree of orientation. By stopping the degree of orientation, I can still produce a balloon that has high burst strength (greater than 20 atm. burst when the wall thickness is between 0.0005"–0.0008") but will behave as a nondistensible balloon up to a certain working pressure and then behave as a distensible balloon when the working pressure is increased.

Such a balloon has the advantage of not exceeding a certain diameter when doing angioplasty so as to prevent any damage to tissue that is not involved in the lesion, such as the medial layer of the artery, while still having the ability to increase its diameter slightly (about 10%) when it is necessary to push or seat a metallic or nonmetallic stent into the inner wall of the artery.

In one embodiment of the present invention, PET is blended with a polyester copolymer having elastomeric characteristics. Inasmuch as both polymers are polyester and have similar melting points, they blend and extrude into tubular form very well. Although an elastomeric copolymer of polyester is used, other similar polymers can be used. However, it is important to stop the biaxial orientation before the balloon is fully oriented when formed. The percentage of the copolymer used will have an effect on the ultimate burst strength of the balloon. But in order to maintain sufficient burst strength, I have determined that a 25% copolyester would be optimal. It is to be noted, however, that up to 50% copolyester can be used to obtain different burst strength distensibility. At the same time it is important to stop the orientation at a level so that when the balloon is formed, the PET polyester component provides substantial burst strength characteristics and nondistensibility characteristic up to a certain working pressure and the copolyester component provides the distensibility characteristics.

This effect can be achieved in the manner to be described below. The effect can be obtained whether there is a blend of materials, as described, or an individual material, such as PET. For example, in the case of using exclusively PET, a standard for full biaxial orientation is defined by taking a tube and measuring its initial inside and outside diameters, referred to respectively as $d_i$ and $d_o$. The final finished diameter of the blown balloon is referred to as D. Thus, for a specific ratio of $D:d_i$, a stretch ratio is defined. The value of D is arbitrarily determined for a given application so that a variety of values of $d_i$ will result in given stretch ratios below the targeted level representing full biaxial orientation. Thus, this is but one example. For PET, a first step is to determine the stretch ratio around which the finished balloon will be substantially fully biaxially oriented. Thus, for PET, a value of $d_i$ of 0.018", $d_o$ of 0.040", and D of 0.120" yields a stretch ratio of 0.120÷0.018 which equals 6.6. This represents the stretch ratio for full biaxial orientation. Having set a benchmark level using the stretch ratio for a given material such as PET, a balloon having the desired characteristics of the present invention can be produced by fixing a value for D and controlling the value of $d_i$ so that the resulting stretch ratio is less than the benchmark level obtained for the stretch ratio which represents substantially full biaxial orientation. Thus, in the present example, if D is held at 0.120", it is desired to make $d_i$ greater than 0.018".

Figure 3:
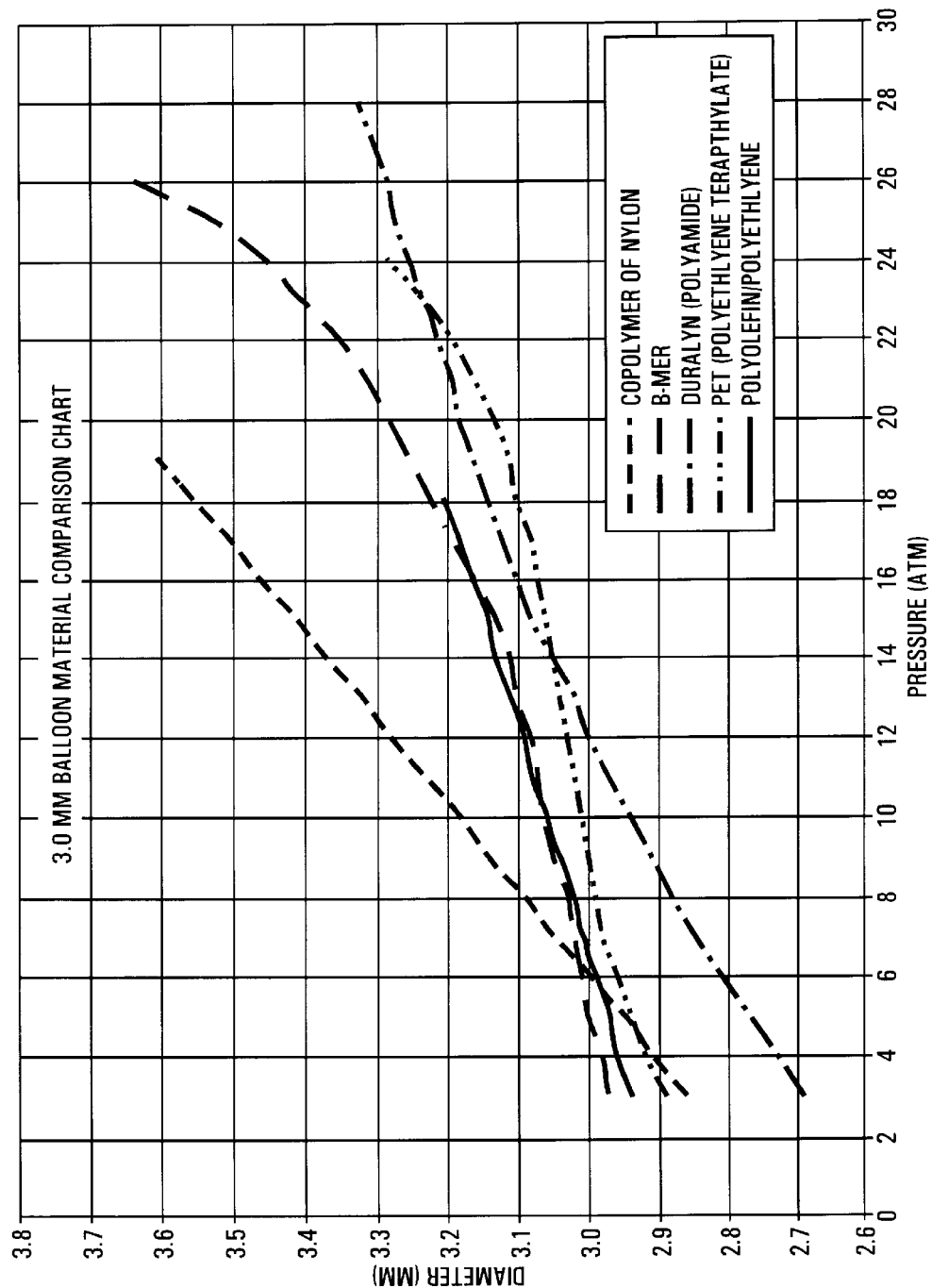
FIG. 3 is a graph of diameter of balloon v. pressure for balloons in the art.
Figure 4:
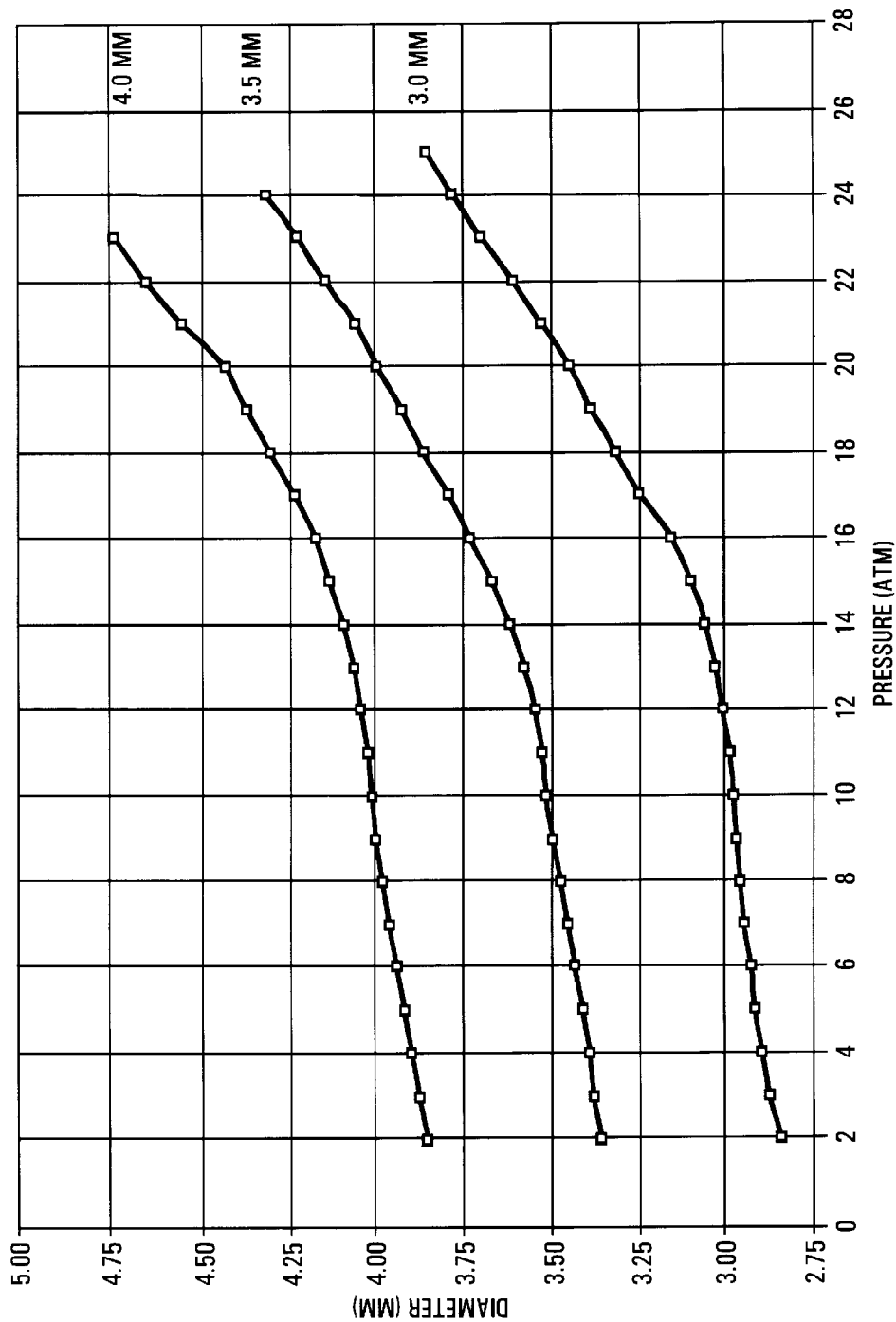
FIG. 4 is a graph of diameter of balloon vs. Pressure for the balloon of the present invention.
Figure 7:
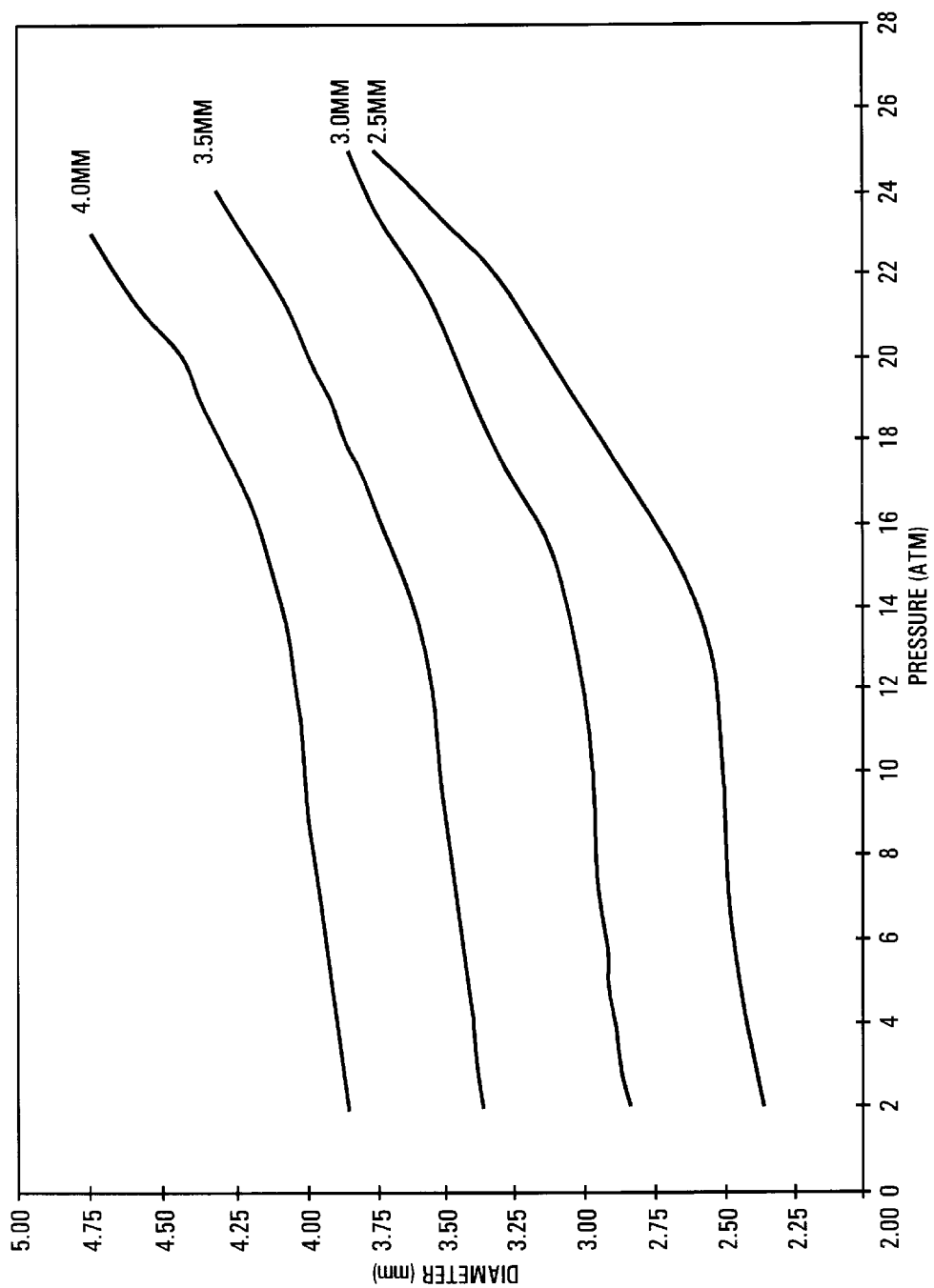
FIG. 7 shows how, for a given size, the distension rate can be varied using the present invention, shown for sizes 2.5–4.0 mm.

The same technique can be applied when making a blend, such as, for example, 75% by weight PET and 25% copolyester. In this example, the copolyester can be obtained from DuPont as product called Hytrel No. 7246. The PET can be obtained from Shell Chemical as product No. 7207. For this blend, it has been determined that a stretch ratio of approximately 6.6 is a close indicator of full biaxial orientation. Thus, following on the previous example of 100% PET, if the balloon diameter D is arbitrarily fixed at 0.120", then the internal diameter of the tube from which the balloon is made, or $d_i$, would be greater than 0.018". Once again, keeping these parameters as described will result in a balloon which is of high burst strength and of minimal distensibility until a predetermined pressure range is reached, at which point the distensibility increases. FIG. 3 shows this relationship in the line on the graph labeled B-MER. FIG. 7 also illustrates this change in distensibility at a predetermined pressure range.

It should be noted that by using different values of $d_i$ for a given D, a greater degree of distensibility can be built into the product above a predetermined pressure range. Thus, by employing stretch ratios progressively smaller than the target stretch ratio which represents full biaxial orientation, the distensibility feature can be enhanced without substantial sacrifice in overall burst pressure rating. The rated burst pressure can be adjusted by changing the percentage of copolyester or other similar polymer used in the blend.

Figure 5:
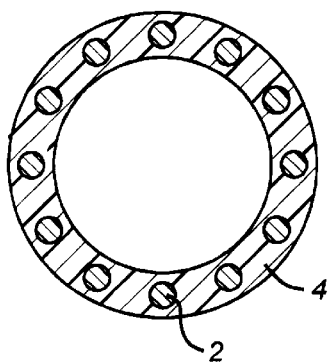
FIG. 5 is a cross-section of the extruded tube.
Figure 6:
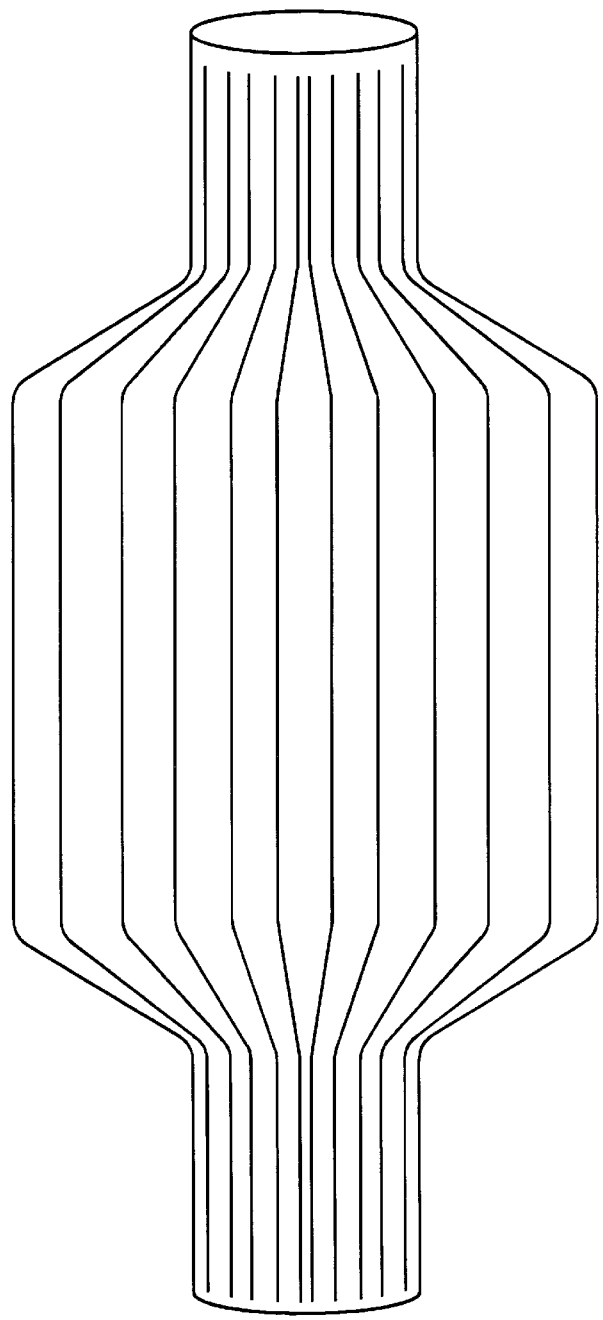
FIG. 6 is a diagrammatic presentation of the balloon with reinforcement.

Another variation of the present invention is to form a composite tube made from PET and copolyester or similar materials that would have chemical affinity to PET such as nylon, polyurethane, PVC and even polyethylene or polypropylene in which a tube is extruded such that there are strands of PET embedded in the matrix of the other polymer. A cross-section of such a composite is shown in FIG. 5. The PET 2 comprises the strands and the matrix 4 is the other polymer.

A value of the stretch ratio that represents complete biaxial orientation is first determined. This value produces the strongest, least distensible design. From that point, the value of D as before is fixed, and the value of $d_i$ is controlled to give a stretch ratio less than the value representing full biaxial orientation. It should be noted that in all the given examples, the longitudinal applied stretch is kept constant and the only variable is $d_i$.

In the second example, using a blend, a $d_i$ of 0.022" yields the desired strength and distensibility rates at different pressures. Using that same blend for a strand design is accomplished by using PET in the strands and the copolyester in the matrix, as shown in FIG. 5. The inside diameter $d_i$ can be 0.020", $d_o$ can be 0.042", the strands can have a diameter of 0.007", and 8–16 strands can be used. A value of D is selected so that the stretch ratio is less than the previously determined value for full biaxial orientation, i.e., in this example, about 6.6. The end result is a high burst pressure and differing rates of distensibility at different pressure ranges. The higher the number of strands of PET, the stronger is the balloon, as well as being less distensible.

In the above situation, when the balloon is formed, the stretch ratio can be adjusted such that all the PET strands are fully stretched to impart very high strength, i.e., using $d_i$ determined in an experiment where the tube is solely made from PET. Afterwards, the stretch ratio can be decreased to reduce the degree of orientation.

Another way to decrease the degree of orientation is to decrease the number of strands of PET in the composite tube. The more strands of PET and the larger the diameter of the PET strand, the stronger the final balloon will be and also the less distensible. By reducing the number of strands and reducing the diameter, the distensibility above a certain pressure will be higher (>10%). If polyethylene is used as the matrix, the composite tube should be irradiated by a cobalt source or by electron beam radiation to cross-link the polyethylene before the balloon is made.

The cross-section of the PET strand can be circular, rectangular, or of any other shape. The matrix can be reversed, so that the strands are of other material such as nylon or polyethylene and the matrix is PET. During the molding process, the balloon molding pressure is normally 50–100 psig. It should be noted not to use excessive pressure in order not to damage the polymer links by overextending the diameter during the blow molding phase of the balloon manufacture. However, use of the technique described above is less likely to do such damage to the molecular chains of the composite or blended polymer.

Some variability can be introduced due to lengthwise stretch. Lengthwise stretch is harder to control due to variations as to the exact section being heated when blowing the balloon. The section of the tube heated so as to soften it in preparation for blowing the balloon depends on the temperature of the heat source and the time of heat source.

Those balloon makers of ordinary skill in this art know the temperature and time necessary to soften the tube to blow the balloon. The heat input (time, and temperature) will determine the blow pressure requirement. The more heat input to the tube, the less pressure is required to blow the balloon and vice versa.

The polyester used in this invention is from Shell Chemical #7207 and the copolyester used is from DuPont material Hytrel #7246, although other materials of similar properties can be used to achieve similar results. Thus, a blend of a highly crystalline material, such as PET or nylon, with a less crystalline material, such as PU or copolyester, is within the scope of the invention. In general, a mixture of a highly crystalline material with an amorphous material is one combination.

It is preferred when blending to limit the less crystalline material to no more than 50% by weight and to target a stretch ratio that is smaller than the value previously determined for that blend to represent substantially complete biaxial orientation, and to use as a lower value of the target stretch ratio a value consistent with burst requirements for the application.

The foregoing disclosure and description of the invention are illustrative and explanatory thereof, and various changes in the size, shape and materials, as well as in the details of the illustrated construction, may be made without departing from the spirit of the invention.

I claim:

1. A dilution balloon catheter having multiple distensibilities for use in surgical procedures, comprising:

a catheter body;

a balloon on said body wherein said balloon has a lower rate of distensibility at a predetermined pressure level;

said balloon having a higher rate of distensibility when said pressure level is increased; and said balloon is made of a single polymeric material which is oriented during fabrication to a level below that level previously determined for that material to be representative of substantially full biaxial orientation.

2. The catheter of claim 1, wherein:

said balloon material is radially expanded during fabrication to a stretch ratio lower than a stretch ratio initially determined to represent substantially complete biaxial orientation for that material.

3. The catheter of claim 2, wherein:

said blend of balloon materials is longitudinally expanded during fabrication to a stretch ratio lower than a stretch ratio initially determined to represent substantially complete biaxial orientation for said blend.

4. A dilution balloon catheter having multiple distensibilities for use in surgical procedures, comprising:

a catheter body;

a balloon on said body wherein said balloon has a lower rate of distensibility at a predetermined pressure level;

said balloon having a higher rate of distensibility when said pressure level is increased; and said balloon is made of a blend of polymeric material which is oriented during fabrication to a level below that level previously determined for that blend to be representative of substantially full biaxial orientation.

5. The catheter of claim 4, wherein:

said blend comprises PET and a copolyester.

6. The catheter of claim 5, wherein:

said blend comprises a copolyester in the range of greater than 0% to less than about 50% by weight of said blend.

7. The catheter of claim 4, wherein:

said blend comprises a highly crystalline material combined with a less crystalline material.

8. The catheter of claim 4, wherein:

said blend of balloon materials is radially expanded during fabrication to a stretch ratio lower than a stretch ratio initially determined to represent substantially complete biaxial orientation for said blend.

9. The catheter of claim 8, wherein:

said blend of balloon materials is substantially similarly stretched longitudinally during fabrication when establishing the target stretch ratio for said blend as when the said blend of balloon materials are used to make the finished balloon.

10. A dilution balloon catheter having multiple distensibilities for use in surgical procedures, comprising:

a catheter body;

a balloon on said body wherein said balloon has a lower rate of distensibility at a predetermined pressure level;

said balloon having a higher rate of distensibility when said pressure level is increased; and said balloon comprises two different materials, with one of said materials extending in at least one longitudinal strand in a matrix of the other material.

11. The catheter of claim 10, wherein:

said strand comprises a highly crystalline material and said matrix comprises a less crystalline material.

12. The catheter of claim 11, wherein:

said strand and matrix are oriented during fabrication to a level below that level previously determined for that material combination and configuration to be representative of substantially full biaxial orientation.

13. The catheter of claim 12, wherein:

said matrix comprises a range of greater than 0% up to about 50% by weight of the balloon.

14. The catheter of claim 13, wherein:

said strand comprises PET and said matrix comprises a copolyester.

15. The catheter of claim 14, wherein:

said balloon comprises a plurality of strands.

16. The catheter of claim 10, wherein:

said matrix comprises a highly crystalline material and said strand comprises a less crystalline material.

* * * * *